(12) United States Patent
Soloveichik et al.

(10) Patent No.: US 6,465,675 B1
(45) Date of Patent: Oct. 15, 2002

(54) METHOD AND CATALYST SYSTEM FOR PRODUCING AROMATIC CARBONATES

(75) Inventors: Grigorii Lev Soloveichik, Latham, NY (US); Kirill Vladimirovich Shalyaev, Clifton Park, NY (US); Marsha Mottel Grade, Niskayuna, NY (US); Bruce Fletcher Johnson, Scotia, NY (US)

(73) Assignee: General Electric Company, Niskayuna, NY (US)

( * ) Notice: Subject to any disclaimer, the term of this patent is extended or adjusted under 35 U.S.C. 154(b) by 26 days.

(21) Appl. No.: 09/677,487

(22) Filed: Oct. 2, 2000

(51) Int. Cl.[7] .................. C07C 69/96; B01J 23/00; B01J 23/42
(52) U.S. Cl. .............. 558/274; 558/272; 502/325; 502/339
(58) Field of Search .............. 558/274, 272; 502/325, 339

(56) References Cited

U.S. PATENT DOCUMENTS

| | | |
|---|---|---|
| 4,187,242 A | 2/1980 | Chalk |
| 5,231,210 A | 7/1993 | Joyce et al. |
| 5,235,087 A | 8/1993 | Klausener et al. |
| 5,239,106 A | 8/1993 | Shafer |
| 5,284,964 A | 2/1994 | Pressman et al. |
| 5,373,083 A | 12/1994 | King et al. |
| 5,380,907 A | 1/1995 | Mizukami et al. |
| 5,399,734 A | 3/1995 | King et al. |
| 5,498,789 A | 3/1996 | Takagi et al. |
| 5,502,232 A | 3/1996 | Buysch et al. |
| 5,543,547 A | 8/1996 | Iwane et al. |
| 5,625,091 A | 4/1997 | Buysch et al. |
| 5,726,340 A | 3/1998 | Takagi et al. |
| 5,760,272 A | 6/1998 | Pressman et al. |
| 5,821,377 A | 10/1998 | Buysch et al. |
| 5,856,554 A | 1/1999 | Buysch et al. |
| 5,917,077 A | 6/1999 | Chaudhari et al. |
| 6,001,768 A * | 12/1999 | Buysch et al. .............. 502/230 |
| 6,114,564 A | 9/2000 | Pressman et al. |
| 6,172,254 B1 | 1/2001 | Pressman et al. |
| 6,180,812 B1 | 1/2001 | Johnson et al. |
| 6,215,014 B1 * | 4/2001 | Johnson et al. .............. 558/274 |

FOREIGN PATENT DOCUMENTS

| | | |
|---|---|---|
| EP | 071286 | 2/1983 |
| EP | 0663388 | 7/1995 |
| EP | 736325 | 3/1996 |
| GB | 1102566 | 2/1968 |
| JP | 94-271506 | 9/1994 |
| JP | 94-271509 | 9/1994 |
| JP | 95-145107 | 6/1995 |
| JP | 96-89810 | 4/1996 |
| JP | 96-92168 | 4/1996 |
| JP | 96-193056 | 7/1996 |
| JP | 97-110804 | 4/1997 |
| JP | 97-255629 | 9/1997 |
| JP | 97-278715 | 10/1997 |
| JP | 97-278716 | 10/1997 |
| JP | 10-158221 | 6/1998 |
| JP | 10-316627 | 12/1998 |

OTHER PUBLICATIONS

Application Serial No. 09/383,424, filed Aug. 27, 1999, "Catalyst Composition and Method for Producing Diaryl Carbonates", Bruce Fletcher Johnson et al.

* cited by examiner

Primary Examiner—T. A. Solola
Assistant Examiner—Ebenezer Sackey
(74) Attorney, Agent, or Firm—S. Bruce Brown; Noreen C. Johnson

(57) ABSTRACT

A method and catalyst system for economically producing aromatic carbonates from aromatic hydroxy compounds. In one embodiment, the present invention provides a method of carbonylating aromatic hydroxy compounds by contacting at least one aromatic hydroxy compound with oxygen and carbon monoxide in the presence of a carbonylation catalyst system that includes an effective amount of a Group VIII B metal source; an effective amount of a bromide composition; an effective amount of an activating organic solvent; an effective amount of a combination of inorganic co-catalysts comprising a lead source and a copper source; and an effective amount of a base.

23 Claims, 1 Drawing Sheet

METHOD AND CATALYST SYSTEM FOR PRODUCING AROMATIC CARBONATES

BACKGROUND OF THE INVENTION

1. Field of the Invention

The present invention is directed to a method and catalyst system for producing aromatic carbonates and, more specifically, to a method and catalyst system for producing diaryl carbonates through the carbonylation of aromatic hydroxy compounds.

2. Discussion of Related Art

Aromatic carbonates find utility, inter alia, as intermediates in the preparation of polycarbonates. For example, a popular method of polycarbonate preparation is the melt transesterification of aromatic carbonates with bisphenols. This method has been shown to be environmentally superior to previously used methods which employed phosgene, a toxic gas, as a reagent and chlorinated aliphatic hydrocarbons, such as methylene chloride, as solvents.

Various methods for preparing aromatic carbonate monomers have been previously described in the literature and/or utilized by industry. A method that has enjoyed substantial popularity in the literature involves the direct carbonylation of aromatic hydroxy compounds with carbon monoxide and oxygen. In general, practitioners have found that the carbonylation reaction requires a rather complex catalyst system. For example, in U.S. Pat. No. 4,187,242, which is assigned to the assignee of the present invention, Chalk reports that a carbonylation catalyst system should contain a Group VIII B metal, such as ruthenium, rhodium, palladium, osmium, iridium, platinum, or a complex thereof. Further refinements to the carbonylation reaction include the identification of organic co-catalysts, such as terpyridines, phenanthrolines, quinolines and isoquinolines in U.S. Pat. No. 5,284,964 and the use of certain halide compounds, such as quaternary ammonium or phosphonium halides in U.S. Pat. No. 5,399,734, both patents also being assigned to the assignee of the present invention.

The economics of the carbonylation process are strongly dependent, inter alia, on the number of moles of aromatic carbonate produced per mole of Group VIII B metal utilized (i.e. "catalyst turnover"). Consequently, much work has been directed to the identification of efficacious inorganic co-catalysts that increase catalyst turnover. In U.S. Pat. No. 5,231,210, which is also assigned to General Electric Company, Joyce et al. report the use of a cobalt pentadentate complex as an inorganic co-catalyst ("IOCC"). In U.S. Pat. No. 5,498,789, Takagi et al. report the use of lead as an IOCC. In U.S. Pat. No. 5,543,547, Iwane et al. report the use of trivalent cerium as an IOCC. In U.S. Pat. No. 5,726,340, Takagi et al. report the use of lead and cobalt as a binary IOCC system.

Further complexity was added to carbonylation catalyst systems by Buysch et al. in U.S. Pat. No. 5,502,232, which ostensibly teaches the use of a quaternary salt, a cocatalyst, a base, and a desiccant in a supported Pd-based carbonylation system. In U.S. Pat. No. 5,821,377, Buysch et al. report the use of said aforementioned catalyst system with the Pd and the cocatalyst provided on the same support.

The literature is virtually silent, however, as to the role of various catalyst system components, such as IOCCs and onium halides for example, in the carbonylation reaction (i.e., the reaction mechanism). Accordingly, meaningful guidance regarding the identification of additional catalyst systems is cursory at best. It would be desirable to identify catalyst systems that would minimize consumption of costly components (e.g., palladium and onium halides) or perhaps that would omit these components. It would also be desirable to minimize the aforementioned consumption of costly components while increasing selectivity toward desirable products and minimizing formation of undesirable byproducts (e.g., 2- and 4-bromophenols). Unfortunately, due to the lack of guidance in the literature, the identification of effective carbonylation catalyst systems has become a serendipitous exercise.

As the demand for high performance plastics continues to grow, new and improved methods of providing product more economically are needed to supply the market. In this context, various processes and catalyst systems are constantly being evaluated; however, the identities of improved and/or additional effective catalyst systems for these processes continue to elude the industry. Consequently, a long felt, yet unsatisfied need exists for new and improved methods and catalyst systems for producing aromatic carbonates and the like.

SUMMARY OF THE INVENTION

Accordingly, the present invention is directed to a method and catalyst system for producing aromatic carbonates. In one embodiment, the present invention provides a method of carbonylating aromatic hydroxy compounds by contacting at least one aromatic hydroxy compound with oxygen and carbon monoxide in the presence of a carbonylation catalyst system that includes an effective amount of a Group VIII B metal source; an effective amount of a bromide composition; an effective amount of an activating organic solvent; an effective amount of a combination of inorganic co-catalysts comprising a lead source and a copper source; and an effective amount of a base.

In various alternative embodiments, the carbonylation catalyst system can include an effective amount of a palladium source and an effective amount of an alkaline metal bromide salt. Further alternative embodiments can include an effective amount of a polyether.

BRIEF DESCRIPTION OF THE DRAWING

Various features, aspects, and advantages of the present invention will become more apparent with reference to the following description, appended claims, and accompanying drawing, wherein the FIG. 1 is a schematic view of a device capable of performing an aspect of an embodiment of the present invention.

DETAILED DESCRIPTION OF PREFERED EMBODIMENTS

Figure 1:
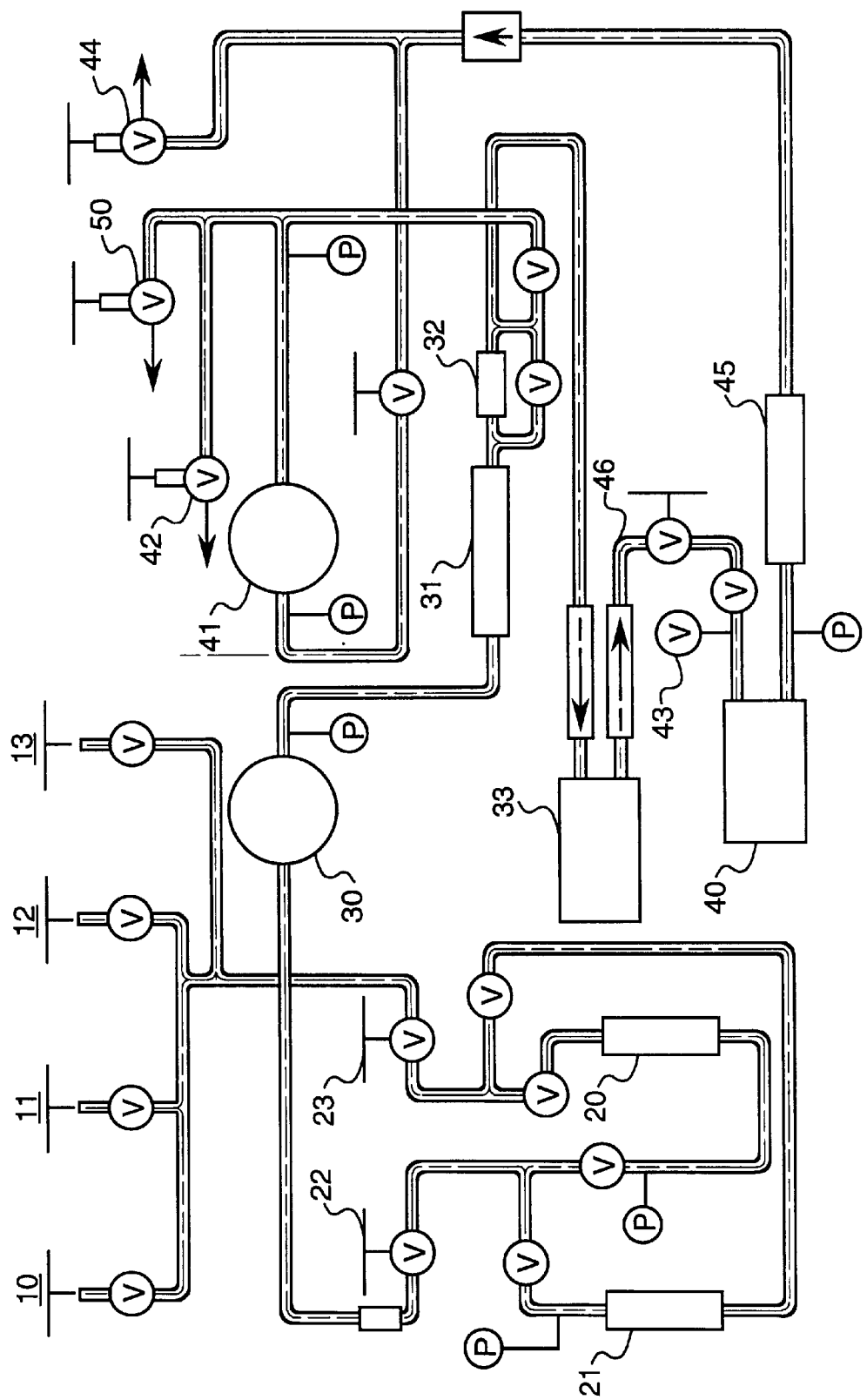

The present invention is directed to a method and catalyst system for producing aromatic carbonates. In one embodiment, the method includes the step of contacting at least one aromatic hydroxy compound with oxygen and carbon monoxide in the presence of a carbonylation catalyst system that includes an effective amount of a Group VIII B metal source; an effective amount of a bromide composition; an effective amount of an activating organic solvent; an effective amount of a combination of inorganic co-catalysts comprising a lead source and a copper source; and an effective amount of a base.

Unless otherwise noted, the term "effective amount," as used herein, includes that amount of a substance capable of either increasing (directly or indirectly) the yield of the carbonylation product or increasing selectivity toward an aromatic carbonate. Optimum amounts of a given substance can vary based on reaction conditions and the identity of other constituents yet can be readily determined in light of the discrete circumstances of a given application.

Aromatic hydroxy compounds which may be used in the practice of the present invention include aromatic mono or polyhydroxy compounds, such as phenol, cresol, xylenol, resorcinol, hydroquinone, and bisphenol A. Aromatic organic mono hydroxy compounds are preferred, with phenol being more preferred.

In various preferred embodiments, the carbonylation catalyst system contains at least one constituent from the Group VIII B metals or a compound thereof. A preferred Group VIII B constituent is an effective amount of a palladium source. In various embodiments, the palladium source may be in elemental form, or it may be employed as a palladium compound. Accordingly, palladium black or elemental palladium deposited on carbon may be used as well as palladium halides, nitrates, carboxylates, oxides and palladium complexes containing carbon monoxide, amines, phosphines or olefins. As used herein, the term "complexes" includes coordination or complex compounds containing a central ion or atom. The complexes may be nonionic, cationic, or anionic, depending on the charges carried by the central atom and the coordinated groups. Other common names for these complexes include complex ions (if electrically charged), Werner complexes, and coordination complexes.

In various applications, it may be preferable to utilize palladium(II) salts of organic acids, including carboxylates with $C_{2-6}$ aliphatic acids. Palladium(II) acetylacetonate is a suitable palladium source. Preferably, the amount of Group VIII B metal source employed should be sufficient to provide about 1 mole of metal per 800–10,000 moles of aromatic hydroxy compound. More preferably, the proportion of Group VIII B metal source employed should be sufficient to provide about 1 mole of metal per 2,000–5,000 moles of aromatic hydroxy compound.

The carbonylation catalyst system further contains an effective amount of a bromide composition, such as an organic bromide salt. The salt may be a quaternary ammonium or phosphonium salt, or a hexaalkylguanidinium bromide. In various embodiments, α, ω-bis (pentaalkylguanidinium)alkane salts may be preferred. Suitable organic bromide compositions include tetrabutylammonium bromide, tetraethylammonium bromide, and hexaethylguanidinium bromide. In preferred embodiments, the carbonylation catalyst system can contain between about 5 and about 2000 moles of bromide per mole of palladium employed, and, more preferably, between about 50 and about 1000 molar equivalents of bromide are used.

In preferred embodiments, the bromide composition can be chosen from various alkaline metal bromide salts. As used herein, the term "alkaline metal" includes the elements of Group I of the Periodic Table ("alkali metals") as well as the elements of Group II ("alkaline-earth metals"). Accordingly, a non-exclusive listing of preferred alkaline metal bromide salts includes lithium bromide, sodium bromide, potassium bromide, and cesium bromide.

The carbonylation catalyst system includes an effective amount of an activating organic solvent, preferably in an amount between about 1% and about 25% by weight. Preferred activating organic solvents include polyethers; i.e., compounds containing two or more C—O—C linkages. The polyether used is preferably free from hydroxy groups to maximize its desired activity and avoid competition with the aromatic hydroxy compound in the carbonylation reaction. Preferred polyethers contain two or more (O—C—C) units.

The polyether may be aliphatic or mixed aliphatic-aromatic. As used in the identification of the polyether, the term "aliphatic" refers to the structures of hydrocarbon groups within the molecule, not to the overall structure of the molecule. Thus, "aliphatic polyether" includes heterocyclic polyether molecules containing aliphatic groups within their molecular structure. Illustrative aliphatic polyethers include diethylene glycol dimethyl ether ("diglyme"); triethylene glycol dimethyl ether ("triglyme"); tetraethylene glycol dimethyl ether ("tetraglyme"); polyethylene glycol dimethyl ether; and crown ethers such as 15-crown-5 (1,4,7,10,13-pentaoxacyclopentadecane) and 18-crown-6 (1,4,7,10,13,16-hexaoxacyclooctadecane). Illustrative mixed aliphatic-aromatic polyethers include diethylene glycol diphenyl ether and benzo-1 8-crown-6.

In alternative embodiments, the activating organic solvent can be a nitrile. Suitable nitrile promoters for the present method include $C_{2-8}$ aliphatic or $C_{7-10}$ aromatic mono- or dinitriles. Illustrative mononitriles include acetonitrile, propionitrile, and benzonitrile. Illustrative dinitriles include succinonitrile, adiponitrile, and benzodinitrile. Mononitriles are generally preferred; more specifically preferred is acetonitrile. It is noted that the function of the nitrile promoter in the present method is not that of an inert solvent. Rather, the nitrile is an active catalyst component that improves the yield of or selectivity toward the aromatic carbonate.

In further alternative embodiments, the activating organic solvent can be a carboxylic acid amide. Fully substituted amides (containing no NH groups including the amide nitrogen) are preferred. Aliphatic, aromatic or heterocyclic amides may be used. Illustrative amides are dimethylformamide, dimethylacetamide (hereinafter sometimes "DMA"), dimethylbenzamide and NMP. Particularly preferred are NMP and DMA.

The activating organic solvent can be a sulfone, which may be aliphatic, aromatic or heterocyclic. Illustrative sulfones are dimethyl sulfone, diethyl sulfone, diphenyl sulfone and sulfolane (tetrahydrothiophene-1,1-dioxide). Of these, sulfolane is often preferred.

The carbonylation catalyst system includes an effective amount of a combination of inorganic co-catalysts (IOCCs) comprising a lead source and a copper source. Additional IOCCs may be used in the carbonylation catalyst system, provided the additional IOCC does not deactivate (i.e. "poison") the original IOCC combination. A non-exclusive listing of additional IOCCs includes titanium, cerium, iron, ytterbium, zinc, manganese, europium, bismuth, nickel, cobalt, zirconium, iridium, rhodium, ruthenium, chromium, and yttrium.

An IOCC can be introduced to the carbonylation reaction in various forms, including salts and complexes, such as tetradentate, pentadentate, hexadentate, or octadentate complexes. Illustrative forms may include oxides, halides, carboxylates, diketones (including beta-diketones), nitrates, complexes containing carbon monoxide or olefins, and the like. Suitable beta-diketones include those known in the art as ligands for the IOCC metals of the present invention. Examples include, but are not limited to, acetylacetone, benzoylacetone, dibenzoylmethane, diisobutyrylmethane, 2,2-dimethylheptane-3,5-dione, 2,2,6-trimethylheptane-3,5-dione, dipivaloylmethane, and tetramethylheptanedione. The quantity of ligand is preferably not such that it interferes with the carbonylation reaction itself, with the isolation or purification of the product mixture, or with the recovery and reuse of catalyst components (such as palladium). An IOCC may be used in its elemental form if sufficient reactive surface area can be provided. In embodiments employing supported palladium, it is noted that the IOCC provides a discrete, catalytic source of metal in a form favorable for such catalysis.

IOCCs are included in the carbonylation catalyst system in effective amounts. In this context an "effective amount" is an amount of IOCC (or combination of IOCCs) that increases the number of moles of aromatic carbonate produced per mole of Group VIII B metal utilized; increases the number of moles of aromatic carbonate produced per mole of bromide utilized; or increases selectivity toward aromatic carbonate production beyond that obtained in the absence of the IOCC (or combination of IOCCs). Optimum amounts of an IOCC in a given application will depend on various factors, such as the identity of reactants and reaction conditions. For example, when palladium is included in the reaction, the molar ratio of lead relative to palladium at the initiation of the reaction is preferably between about 0.1 and about 150, and the molar ratio of copper relative to palladium is preferably between about 0.1 and about 15.

The carbonylation catalyst system also includes an effective amount of a base. In this context, the term "effective amount" carries the same definition as it does relative to IOCCs. Any desired bases or mixtures thereof, whether organic or inorganic may be used. A non-exclusive listing of suitable inorganic bases include alkali metal hydroxides and carbonates; $C_2$–$C_{12}$ carboxylates or other salts of weak acids; and various alkali metal salts of aromatic hydroxy compounds, such as alkali metal phenolates. Hydrates of alkali metal phenolates may also be used. Examples of suitable organic bases include tertiary amines and the like. In various alternative embodiments, the base used is an alkali metal salt incorporating an aromatic hydroxy compound, more preferably an alkali metal salt incorporating the aromatic hydroxy compound to be carbonylated to produce the aromatic carbonate. A nonexclusive listing of suitable bases includes sodium phenoxide and sodium hydroxide. In preferred embodiments, between about 5 and about 1000 molar equivalents of base are employed (relative to palladium), and, more preferably, between about 100 and about 400 molar equivalents of base are used.

The carbonylation reaction can be carried out in a batch reactor or a continuous reactor system. Due in part to the low solubility of carbon monoxide in organic hydroxy compounds, such as phenol, it is preferable that the reactor vessel be pressurized. In preferred embodiments, gas can be supplied to the reactor vessel in proportions of between about 2 and about 50 mole percent oxygen, with the balance being carbon monoxide. In all occurrences, the mole percent oxygen supplied is below the explosion range for safety reasons. Additional gases may be present in amounts that do not deleteriously affect the carbonylation reaction. The gases may be introduced separately or as a mixture. A total pressure in the range of between about 10 and about 250 atmospheres is preferred. Drying agents, typically molecular sieves, may be present in the reaction vessel. Reaction temperatures in the range of between about 60° C. and about 150° C. are preferred. Gas sparging or mixing can be used to aid the reaction.

In order that those skilled in the art will be better able to practice the present invention reference is made to the FIGURE, which shows an example of a continuous reactor system for producing aromatic carbonates. The symbol "V" indicates a valve and the symbol "P" indicates a pressure gauge.

The system includes a carbon monoxide gas inlet 10, an oxygen inlet 11, a manifold vent 12, and an inlet 13 for a gas, such as carbon dioxide. A reaction mixture can be fed into a low pressure reservoir 20, or a high pressure reservoir 21, which can be operated at a higher pressure than the reactor for the duration of the reaction. The system further includes a reservoir outlet 22 and a reservoir inlet 23. The gas feed pressure can be adjusted to a value greater than the desired reactor pressure with a pressure regulator 30. The gas can be purified in a scrubber 31 and then fed into a mass flow controller 32 to regulate flow rates. The reactor feed gas can be heated in a heat exchanger 33 having appropriate conduit prior to being introduced to a reaction vessel 40. The reaction vessel pressure can be controlled by a back pressure regulator 41. After passing through a condenser 25, the reactor gas effluent may be either sampled for further analysis at valve 42 or vented to the atmosphere at valve 50. The reactor liquid can be sampled at valve 43. An additional valve 44 can provide further system control, but is typically closed during the gas flow reaction.

In the practice of one embodiment of the invention, the carbonylation catalyst system and aromatic hydroxy compound are charged to the reactor system. The system is sealed. Carbon monoxide and oxygen are introduced into an appropriate reservoir until a preferred pressure (as previously defined) is achieved. Circulation of condenser water is initiated, and the temperature of the heat exchanger 33 (e.g., oil bath) can be raised to a desired operating temperature. A conduit 46 between heat exchanger 33 and reaction vessel 40 can be heated to maintain the desired operating temperature. The pressure in reaction vessel 40 can be controlled by the combination of reducing pressure regulator 30 and back pressure regulator 41. Upon reaching the desired reactor temperature, aliquots can be taken to monitor the reaction.

EXAMPLES

The following examples are included to provide additional guidance to those skilled in the art in practicing the claimed invention. While some of the examples are illustrative of various embodiments of the claimed invention, others are comparative. The examples provided are merely representative of the work that contributes to the teaching of the present application. Accordingly, these examples are not intended to limit the invention, as defined in the appended claims, in any manner.

As discussed supra, the economics of aromatic carbonate production is dependent on the number of moles of aromatic carbonate produced per mole of Group VIII B metal utilized. In the following examples, the aromatic carbonate produced is diphenylcarbonate (DPC) and the Group VIII B metal utilized is palladium. For convenience, the number of moles of DPC produced per mole of palladium utilized is referred to as the palladium turnover number (Pd TON). Selectivity to DPC was calculated as 0.5 moles DPC produced/(moles phenol charged—moles phenol remaining). Another useful metric was the ratio of DPC (a desired product) to bromophenols (undesired byproducts).

Examples 1–13

All experimental runs were conducted in the reactor system depicted in the FIGURE and described supra. To the reactor at ambient conditions were added phenol (64 g; 680 mmol), lead (II) oxide, copper (II) acetylacetonate, sodium bromide, sodium hydroxide, tetraglyme, and palladium (II) acetylacetonate in varying amounts. Molecular sieves (1/16" diameter pellets, 3 Å, 30 grams) were placed in a perforated polytetrafluoroethylene basket mounted to the stir shaft of the reactor. The reactor vessel was sealed and pressurized to 109 atm. with an 8.9% oxygen in carbon monoxide gas mixture. The reactor was heated to 100° C. over 10 minutes and stirred at 1600 rpm over 2.5 hours while maintaining the reaction conditions. Liquid sampling of the reactor contents was performed every 30 minutes with a sample dip tube. Reaction aliquots were analyzed by HPLC for DPC and bromophenols content. The data listed in the following table represent the highest sampled DPC content for each experimental run. Unless otherwise specified, all parts are by weight, and all equivalents are relative to palladium. The following results were obtained:

| Run | Pd ppm | PbO equiv. | Cu(acac)$_2$ equiv. | NaOH equiv. | NaBr equiv. | tetraglyme wt. % | Pd TON | Selectivity % | DPC: BrC$_6$H$_4$OH |
|---|---|---|---|---|---|---|---|---|---|
| 1 | 24 | 30 | 10 | 286 | 775 | 12 | 6242 | 90 | 42.2 |
| 2 | 23 | 31 | 10 | 305 | 807 | 12 | 7402 | 90 | 38.7 |
| 3 | 24 | 29 | 10 | 300 | 752 | 6 | 4552 | 92 | 69.4 |
| 4 | 23 | 30 | 20 | 360 | 781 | 12 | 5863 | 86 | 33.5 |
| 5 | 23 | 87 | 10 | 279 | 766 | 12 | 6325 | 90 | 58.2 |
| 6 | 24 | 29 | 10 | — | 767 | 12 | 4221 | 71 | 11.8 |
| 7 | 23 | 29 | 10 | 175 | 892 | — | 1935 | 38 | 38.3 |
| 8 | 23 | 29 | 10 | — | 775 | — | 195 | 7 | 1.5 |
| 9 | 13 | — | 10 | 317 | 781 | 6 | 3823 | 50 | 9.3 |
| 10 | 14 | 60 | 10 | 317 | 727 | — | 869 | 14 | 14.2 |
| 11 | 13 | 64 | 10 | — | 780 | 6 | 7760 | 75 | 20.6 |
| 12 | 13 | 63 | — | 317 | 778 | 6 | 7641 | 73 | 21.2 |
| 13 | 13 | 61 | 10 | 290 | 749 | 6 | 7007 | 83 | 56.5 |

The various reaction conditions show that a Pd TON at least as high as 7402 can be obtained utilizing the present catalyst system. Comparison among the runs shows that the present system consistently provides superior performance evidenced by high Pd TON with accompanying high selectivity and DPC:bromophenols ratio. It is also noted that omission of selected components results in significant decreases in selectivity and DPC:bromophenols ratio.

Example 14

The general procedure of Examples 1–13 was repeated with a catalyst system containing tetraethylammonium bromide ("TEAB") instead of sodium bromide to produce the following results:

| Run | Pd ppm | PbO equiv. | Cu(acac)$_2$ equiv. | NaOH equiv. | TEAB equiv. | tetraglyme wt. % | Pd TON | Selectivity % | DPC: BrC$_6$H$_4$OH |
|---|---|---|---|---|---|---|---|---|---|
| 14 | 23 | 29 | 10 | 280 | 782 | 12 | 6945 | 92 | 55.8 |

When compared with previously presented data, it is evident that the performance of systems employing alkaline metal bromide salts can be substantially similar to those employing onium bromide salts. The use of inexpensive alkaline metal bromide salts has the potential to substantially reduce bromide related variable costs. In addition, recovery and recycle of intact alkaline metal bromide is expected to be substantially more efficient, owing to the higher thermal and chemical stability as well as increased water solubility of alkaline metal bromides relative to organic onium bromides.

It will be understood that each of the elements described above, or two or more together, may also find utility in applications differing from the types described herein. While the invention has been illustrated and described as embodied in a method and catalyst system for producing aromatic carbonates, it is not intended to be limited to the details shown, since various modifications and substitutions can be made without departing in any way from the spirit of the present invention. For example, additional effective IOCC compounds can be added to the reaction. As such, further modifications and equivalents of the invention herein disclosed may occur to persons skilled in the art using no more than routine experimentation, and all such modifications and equivalents are believed to be within the spirit and scope of the invention as defined by the following claims.

What is claimed is:

1. A carbonylation catalyst composition, comprising
   a Group VIII B metal source;
   a bromide composition;
   an activating organic solvent selected from the group consisting of a polyether, a nitrile, and a carboxylic acid amide;
   a combination of inorganic co-catalysts comprising a lead source and a copper source; and
   a base.

2. The carbonylation catalyst composition of claim 1, wherein the Group VIII B metal source is a palladium source.

3. The carbonylation catalyst composition of claim 2, wherein the palladium source is a Pd(II) salt or complex.

4. The carbonylation catalyst composition of claim 3, wherein the palladium source is palladium acetylacetonate.

5. The carbonylation catalyst composition of claim 2, wherein the palladium source is palladium metal supported on an inorganic or organic support.

6. The carbonylation catalyst composition of claim 5, wherein the palladium source is palladium on carbon.

7. The carbonylation catalyst composition of claim 1, wherein the bromide composition is an alkaline metal bromide salt.

8. The carbonylation catalyst composition of claim 1, wherein the activating organic solvent is a polyether.

9. The carbonylation catalyst composition of claim 1, wherein the activating organic solvent is a nitrile.

10. The carbonylation catalyst composition of claim 1, wherein the activating organic solvent is a carboxylic acid amide.

11. The carbonylation catalyst composition of claim 2, wherein the molar ratio of lead relative to palladium is between about 0.1 and about 150.

12. The carbonylation catalyst composition of claim 2, wherein the molar ratio of copper relative to palladium is between about 0.1 and about 15.

13. A carbonylation catalyst composition, comprising
   a Group VIII B metal source;
   a bromide composition;
   a polyether;
   a combination of inorganic co-catalysts comprising a lead source and a copper source; and
   a base.

14. The carbonylation catalyst composition of claim 13, wherein the Group VIII B metal source is a palladium source.

15. The carbonylation catalyst composition of claim 14, wherein the palladium source is a Pd(II) salt or complex.

16. The carbonylation catalyst composition of claim 15, wherein the palladium source is palladium acetylacetonate.

17. The carbonylation catalyst composition of claim 13, wherein the bromide composition is an alkaline metal bromide salt.

18. The carbonylation catalyst composition of claim 14, wherein the molar ratio of lead relative to palladium is between about 0.1 and about 150.

19. The carbonylation catalyst composition of claim 14, wherein the molar ratio of copper relative to palladium is between about 0.1 and about 15.

20. A carbonylation catalyst composition, comprising
   a palladium source;
   an alkaline metal bromide salt;
   tetraglyme;
   a combination of inorganic co-catalysts comprising a lead source and a copper source; and
   a base.

21. The carbonylation catalyst composition of claim 1, wherein the Group VIII B metal source is present in an amount of about 1 mole of metal per 800–10,000 moles of aromatic hydroxy compound; the bromide composition is present in an amount of between about 5 and about 2000 moles of bromide per mole of the Group VIII B metal source; the organic solvent is present in an amount of about 1–25% by weight; the lead source is present in an amount of about 0.1–150 moles of lead per mole of the Group VIII B metal; the copper source is present in an amount of about 0.1–15 moles of copper per mole of the Group VIII B metal; and base is present in an amount of between about 5 and about 1000 molar equivalents relative to Group VIII B metal.

22. The carbonylation catalyst composition of claim 13, wherein the Group VIII B metal source is present in an amount of about 1 mole of metal per 800–10,000 moles of aromatic hydroxy compound; the bromide composition is present in an amount of between about 5 and about 2000 moles of bromide per mole of the Group VIII B metal source; the polyether is present in an amount of about 1–25% by weight; the lead source is present in an amount of about 0.1–150 moles of lead per mole of the Group VIII B metal; the copper source is present in an amount of about 0.1–15 moles of copper per mole of the Group VIII B metal; and base is present in an amount of between about 5 and about 1000 molar equivalents relative to Group VIII B metal.

23. The carbonylation catalyst composition of claim 20, wherein the palladium source is present in an amount of about 1 mole of metal per 800–10,000 moles of aromatic hydroxy compound; the alkaline metal bromide salt is present in an amount of between about 5 and about 2000 moles of bromide per mole of palladium source; tetraglyme is present in an amount of about 1–25% by weight; the lead source is present in an amount of about 0.1–150 moles of lead per mole of palladium; the copper source is present in an amount of about 0.1–15 moles of copper per mole of palladium; and base is present in an amount of between about 5 and about 1000 molar equivalents relative to palladium.

* * * * *